(12) United States Patent
Gelikonov et al.

(10) Patent No.: US 6,608,684 B1
(45) Date of Patent: Aug. 19, 2003

(54) OPTICAL COHERENT TOMOGRAPHY APPARATUS, FIBEROPTIC LATERAL SCANNER AND METHOD FOR STUDYING BIOLOGICAL TISSUES IN VIVO

(75) Inventors: Valentin M. Gelikonov, Nizhny Novgorod (RU); Grigory V. Gelikonov, Nizhny Novgorod (RU); Natalia D. Gladkova, Nizhny Novgorod (RU); Natalia M. Shahova, Nizhny Novgorod (RU); Felix I. Feldchtein, Nizhny Novgorod (RU); Alexander M. Sergeev, Nizhny Novgorod (RU)

(73) Assignee: Imalux Corporation, Cleveland, OH (US)

( * ) Notice: Subject to any disclaimer, the term of this patent is extended or adjusted under 35 U.S.C. 154(b) by 0 days.

(21) Appl. No.: 09/623,343

(22) PCT Filed: Feb. 9, 1999

(86) PCT No.: PCT/RU99/00034
§ 371 (c)(1),
(2), (4) Date: Dec. 1, 2000

(87) PCT Pub. No.: WO99/45338
PCT Pub. Date: Sep. 10, 1999

(30) Foreign Application Priority Data

Mar. 6, 1998 (RU) .............................. 98104238

(51) Int. Cl.[7] .................................. G01B 9/02
(52) U.S. Cl. ........................................ 356/479
(58) Field of Search ............... 356/477, 479; 250/227.19, 227.27; 600/425

(56) References Cited

U.S. PATENT DOCUMENTS

| 3,941,927 A | 3/1976 | Russell |
| 4,945,239 A | 7/1990 | Wist et al. |
| 5,321,501 A | 6/1994 | Swanson et al. |
| 5,383,467 A | 1/1995 | Auer et al. |
| 5,835,642 A | * 11/1998 | Gelikonov et al. ............ 385/4 |
| 5,867,268 A | * 2/1999 | Gelikonov et al. ......... 356/477 |

FOREIGN PATENT DOCUMENTS

| RU | 94007805 A1 | 5/1996 |
| RU | 2069063 | 11/1996 |

* cited by examiner

Primary Examiner—Samuel A. Turner
Assistant Examiner—Michael A. Lyons
(74) Attorney, Agent, or Firm—Pearne & Gordon LLP

(57) ABSTRACT

The present invention relates to the analysis of the internal structures of objects using optical means. According to the invention there were designed an apparatus suited for optical coherence tomography (OCT), an optical fiber lateral scanner (15), which is a part of said apparatus and is incorporated into an optical fiber probe (8), and a method for studying biological tissue in vivo, which allows for making a diagnostics of the biological tissue under, study on basis of the state of the basal membrane (46). The moving part of lateral scanner (15) of sampling arm (4) of interferometer (2) is arranged comprising a current conductor (19), which envelopes a magnetic system (17) in the area of one of its poles (25) and an optical fiber (13), which is rigidly fastened to current conductor (19), whereas optical fiber (13) serves as a flexible cantilever, allowing to miniaturize the optical fiber probe (8). Constructing magnetic system (17) as two permanent magnets (22, 28) which are aligned at their analogous poles (25, 29), and placing optical fiber (13) in a throughhole (30), the throughhole (30) being formed by the facing grooves made in said analogous poles (25, 29) of permanent magnets (22, 28), ensure optimization of the design of optical fiber probe (8), the body (11) of said optical fiber probe (8) having limited dimensions. Optical fiber probe (8) is placed at the distal end of an instrumental channel of an endoscope or borescope. Studying of biological tissue in vivo with the aid of the developed apparatus allows for non-invasive diagnostics of biological tissue on basis of the state of basal membrane (46).

17 Claims, 6 Drawing Sheets

OPTICAL COHERENT TOMOGRAPHY APPARATUS, FIBEROPTIC LATERAL SCANNER AND METHOD FOR STUDYING BIOLOGICAL TISSUES IN VIVO

TECHNICAL FIELD

The present invention relates to physical engineering, in particular, to the study of internal structure of objects by optical means, and can be applied for medical diagnostics of individual organs and systems of human body in vivo, as well as for industrial diagnostics, for example, control of technological processes.

BACKGROUND ART

In recent years, there has been much research interest in the optical coherence tomography of scattering media, in particular, biological tissues. Optical coherence tomography apparatus are fairly well known and comprise a low coherent light source and an optical interferometer, commonly designed as either a Michelson optical fiber interferometer or a Mach-Zender optical fiber interferometer.

For instance, an optical coherence tomography apparatus known from the paper by X.Clivaz et al., "High resolution reflectometry in biological tissues", OPTICS LETTERS, Vol. 17, No. 1, Jan. 1, 1992, includes a low coherent light source and a Michelson optical fiber interferometer comprising a beam-splitter optically coupled with optical fiber sampling and reference arms. The sampling arm incorporates an optical fiber piezoelectric phase modulator and has an optical probe at its end, whereas the reference arm is provided with a reference mirror installed at its end and connected with a mechanical in-depth scanner which performs step-by-step alteration of the optical length of this arm within a fairly wide range (at least several tens of operating wavelengths of the low coherent light source), which, in turn, provides information on microstructure of objects at different depths. Incorporating a piezoelectric phase modulator in the interferometer arm allows for lock-in detection of the information-carrying signal, thus providing a fairly high sensitivity of measurements.

The apparatus for optical coherence tomography reported in the paper by J. A.Izatt, J. G. Fujimoto et al., Micron-resolution biomedical imaging with optical coherence tomography, Optics & Photonics News, October 1993, Vol. 4, No. 10, p. 14–19 comprises a low coherent light source and an optical fiber interferometer designed as a Michelson interferometer. The interferometer includes a beam-splitter, a sampling arm with a measuring probe at its end, and a reference arm, whose end is provided with a reference mirror, movable at constant speed and connected with an in-depth scanner. This device allows for scanning the difference in the optical lengths of the sampling and reference arms. The information-carrying signal is received in this case using a Doppler frequency shift induced in the reference arm by a constant speed movement of the reference mirror.

Another optical coherence tomography apparatus comprising a low coherent light source and an optical fiber interferometer having a beam-splitter optically coupled to a sampling and reference arms is known from RU Pat. No. 2,100,787, 1997. At least one of the arms includes an optical fiber piezoelectric in-depth scanner, allowing changing of the optical length of said interferometer arm by at least several tens of operating wavelengths of the light source, thus providing information on microstructure of media at different depths. Since □ piezoelectric in-depth scanner is a low-inertia element, this device can be used to study media whose □ harachteristic time for changing of optical characteristics or position relative to the optical probe is very short (the order of a second).

Major disadvantage inherent in all of the above-described apparatus as well as in other known apparatus of this type is that studies of samples in the direction approximately perpendicular to the direction of propagation of optical radiation are performed either by respective moving of the samples under study or by scanning a light beam by means of bulky lateral scanners incorporated into galvanometric probes. This does not allow these devices to be applied for medical diagnostics of human cavities and internal organs in vivo, as well as for industrial diagnostics of hard-to-access cavities. (Further throughout the text, a device performing scans in the direction approximately perpendicular to the direction of propagation of optical radiation is referred to as a "lateral scanner" in contrast to a device that allows for scanning the difference in the optical lengths of interferometer arms referred to as a "in-depth scanner").

Apparatus for optical coherence tomography known from U.S. Pat. No. 5,383,467, 1995 comprises a low coherent light source and an optical interferometer designed as a Michelson interferometer. This interferometer includes a beam-splitter, a sampling arm with an optical fiber sampling probe installed at its end, and a reference arm whose end is provided with a reference mirror connected with an in-depth scanner, which ensures movement of the reference mirror at a constant speed. The optical fiber sampling probe is a catheter, which comprises a single-mode optical fiber placed into a hollow metal tube having a lens system and an output window of the probe at its distal end. The optical tomography apparatus includes also a lateral scanner, which is placed outside the optical fiber probe and performs angular and/or linear scanning of the optical radiation beam in the output window of the optical fiber probe. However, although such geometry allows for introducing the probe into various internal cavities of human body and industrial objects, the presence of an external relative to the optical fiber probe lateral scanner and scanning the difference in the optical lengths of the sampling and reference arms by means of mechanical movement of the reference mirror significantly limit the possibility of using this device for performing diagnostics of surfaces of human cavities and internal organs in vivo, as well as for industrial diagnostics of hard-to-access cavities.

Apparatus for optical coherence tomography known from U.S. Pat. No. 5,582,171, 1996 comprises a low coherent light source and an optical fiber interferometer designed as a Mach-Zender interferometer having optical fiber sampling and reference arms and two beam-splitters. The reference arm includes a unit for changing the optical length of this arm. This unit is designed as a reference mirror with a spiral reflective surface arranged with a capability of rotating and is connected with a driving mechanism that sets the reference mirror in motion. The sampling arm is provided with an optical fiber probe having an elongated metal cylindrical body with a throughhole extending therethrough, and an optical fiber extending through the throughhole. A lateral scanner is placed at the distal end of the probe, which lateral scanner comprises a lens system, a rotatable mirror, and a micromotor for rotating the mirror, whereas an output window of the probe is located in the side wall of the cylindrical body. This device allows imaging of walls of thin vessels, but is unsuitable as a diagnostic means to image surfaces of cavities and internal organs inside a human body, as well as for industrial diagnostics of hard-to-access large-space cavities.

Another optical coherence tomography apparatus is known from U.S. Pat. No. 5,321,501, 1994 and comprises a low coherent light source optically coupled with an optical fiber Michelson interferometer, which includes a beam-splitter and optical fiber sampling and reference arms. The reference arm has a reference mirror mounted at its end and connected with an in-depth scanner. The latter performs movement of the reference mirror at a constant speed, thereby changing the optical length of this arm by at least several tens of operating wavelengths of the light source. The interferometer also comprises a photodetector whose output is connected with a data processing and displaying unit, and a source of control voltage connected with the in-depth scanner. The sampling arm incorporates an optical fiber probe having an elongated body with a throughhole extending therethrough, wherein a sheath with an optical fiber embedded in it extends through the throughhole. The sheath is attached to the stationary body through a pivot joint. The probe body contains also a lateral scanner comprising a bearing support, an actuator, and a lens system. The actuator includes a moving part and a stationary part, whereas the bearing support, the stationary part of the actuator and the lens system are mechanically connected with the probe body. The fiber-carrying sheath rests on the moving part of the actuator. The actuator may be a piezoelectric element, stepper motor, electromagnetic system or electrostatic system. The distal part of the probe body includes a lens system, the end face of the distal part of the optical fiber being optically coupled with the lens system, whereas the actuator is connected with a source of control current. The output of the data processing and displaying unit of the optical fiber interferometer is the output of the apparatus for optical coherence tomography. A disadvantage of this apparatus is that it is not fit for diagnostics of surfaces of hard-to-access internal human organs in vivo, such as, for example, stomach and larynx, and for industrial diagnostics of surfaces of hard-to-reach cavities of technical objects. That is due to the fact that the optical fiber probe in this apparatus must have relatively large dimensions since maximum movement of the optical fiber relative to the size of the actuator cannot be more than 20%, because of the moving part of the actuator being positioned at one side of the fiber-carrying sheath. Besides, the mechanical movement of the reference mirror at a constant speed used for scanning the difference in optical lengths of the reference and sampling arms restricts the range of objects, which can be studied in vivo by this apparatus, or by any other apparatus of this kind, to those objects whose optical characteristics and position relative to the optical probe do not change practically in the process of measurements.

In prior art there are known optical fiber lateral scanners which comprise a stationary part, including a bearing support, an electromagnet, and a lens system, and a moving part including a permanent magnet attached to an optical fiber (see, e.g., U.S. Pat. No. 3,470,320, 1969, U.S. Pat. No. 5,317,148, 1994). In these devices, the optical fiber is anchored at one end to a bearing support and serves as a flexible cantilever, whereas the free end of the optical fiber is arranged such, that it can move in the direction perpendicular to its own axis. The permanent magnet is placed in a gap between the poles of the electromagnet. A disadvantage of devices of this type is that the amplitude of optical fiber deflection is limited by the allowable mass of the magnet fixedly attached to the optical fiber (from the point of view of sagging), and by difficulties in inducing alternate magnetic field of sufficient strength when the device is to have small dimensions.

Another optical fiber lateral scanner according to U.S. Pat. No. 4,236,784, 1979 also comprises a stationary part, which includes a bearing support, an electromagnet, and a lens system, and a moving part, including a permanent magnet. In this device, the permanent magnet is made as a thin film of magnetic material coated onto the optical fiber, whereas the electromagnet is arranged as an array of thin-film conductors on a substrate layer that is placed orthogonal relative to the end face of the optical fiber. In this device the small mass of the magnet limits the strength of the induced field, which, in turn, limits the amplitude of optical fiber deflection. An increase in the amplitude of deflection due to an increase in the field strength is impossible-since this would require currents much exceeding damaging currents for thin-film conductors. Besides, the array of thin-film conductors, being positioned across the direction of propagation of an optical radiation beam, disturbs the continuity of scanning, thus resulting in loss of information.

Another optical fiber lateral scanner comprising a stationary part and a moving part is known from U.S. Pat. No. 3,941,927, 1976. The stationary part comprises a bearing support, a permanent magnet, and a lens system, whereas the moving part includes a current conductor arranged as a conductive coating on the optical fiber. The optical fiber is placed in a gap between the pole pieces of the permanent magnet and fixedly attached to the bearing support so that its free end can move in the direction approximately perpendicular to its own axis, and serves as a flexible cantilever. The end face of the distal part of the optical fiber is optically coupled with the lens system, whereas the current conductor is connected with a source of control current. In this device the field strength induced by the current conductor, when control current is applied, is limited by a small mass of the conductive coating, thus limiting the deflection amplitude of the optical fiber. Due to allocation of the optical fiber between two pole pieces of the permanent magnet, the overall dimensions of the device are relatively large. Thus, a disadvantage of this lateral scanner, as well as of other known lateral scanners, is that it is impossible to provide necessary performance data, in particular, miniature size, simultaneously with required deflection amplitude of the optical fiber to incorporate such a device in an optical fiber probe of an optical fiber interferometer, which is part of a device for optical coherence tomography suited for diagnostics of surfaces of hard-to-access human internal organs in vivo, as well as for industrial diagnostics of hard-to-reach cavities.

A particular attention has been given lately to studies of biological tissues in vivo. For instance, a method for studying biological tissue in vivo is known from U.S. Pat. No. 5,321,501, 1994 and U.S. Pat. No. 5,459,570, 1995, in which a low coherent optical radiation beam at a given wavelength is directed towards a biological tissue under study, specifically ocular biological tissue, and to a reference mirror along the first and the second optical paths, respectively. The relative optical lengths of these optical beam paths are changed according to a predetermined rule; radiation back-scattered from ocular biological tissue is combined with radiation reflected from a reference mirror. The signal of interference modulation of the intensity of the optical radiation, which is a result of this combining, is used to acquire an image of the ocular biological tissue. In a particular embodiment, a low coherent optical radiation beam directed to biological tissue under study is scanned across the surface of said biological tissue.

A method for studying biological tissue in vivo is known from U.S. Pat. No. 5,570,182, 1996. According to this method, an optical radiation beam in the visible or near IR range is directed to dental biological tissue. An image is acquired by visualizing the intensity of scattered radiation. The obtained image is then used for performing diagnostics of the biological tissue. In a particular embodiment, a low coherent optical radiation beam is used, which is directed to dental tissue, said beam being scanned across the surface of interest, and to a reference mirror along the first and second optical paths, respectively. Relative optical lengths of these optical paths are changed in compliance with a predetermined rule; radiation backscattered from the dental tissue is combined with radiation reflected by the reference mirror. A signal of interference modulation of intensity of the optical radiation, which is a result of said combining, is used to visualize the intensity of the optical radiation backscattered from said biological tissue. However, this method, as well as other known methods, is not intended for performing diagnostics of biological tissue covered with epithelium.

DISCLOSURE OF INVENTION

The object of the present invention is to provide an apparatus for optical coherence tomography and an optical fiber lateral scanner which is part of said optical coherence tomography apparatus, with improved performance data, both these devices being suited for diagnostics of soft and hard biotissue in vivo, in particular, for performing diagnostics of human cavity surfaces and human internal organs, for diagnostics of dental, bony, and cartilage biotissues, as well as for industrial diagnostics of hard-to-access cavities of technical objects. Another object of the invention is to provide a method for diagnostics of biotissue in vivo allowing for diagnostics of biotissue covered with epithelium, in particular, of biotissue lining the surface of human internal organs and cavities.

The developed apparatus for optical coherence tomography, similarly to described above apparatus known from U.S. Pat. No. 5,321,501 comprises a low coherent light source and an optical fiber interferometer. The interferometer includes a beam-splitter, a sampling and reference optical fiber arms, a photodetector, a data processing and displaying unit, and a source of control voltage. The beam-splitter, sampling and reference optical fiber arms, and the photodetector are mutually optically coupled, the output of said photodetector being connected with said data processing and displaying unit. At least one of the arms comprises an in-depth scanner having a capability of changing the optical length of said interferometer arm by at least several tens of operating wavelengths of the light source. The sampling arm includes a flexible part, which is made capable of being introduced into an instrumental channel of an endoscope or borescope and is provided with an optical fiber probe having an elongated body with a throughhole extending therethrough, an optical fiber extending through the throughhole, and an optical fiber lateral scanner. The distal part of the optical fiber is arranged to allow for deflection in the direction approximately perpendicular to its own axis. The optical fiber lateral scanner comprises a stationary part mechanically connected with the optical fiber probe body and a moving part. The stationary part includes a bearing support, a magnetic system and a lens system. The end surface of the distal part of the optical fiber is optically coupled with the lens system while the lateral scanner is corrected with a source of control current. The reference arm has a reference mirror installed at its end, whereas the in-depth scanner is connected with a source of control voltage. The output of the data processing and displaying unit is the output of the optical coherence tomography apparatus.

Unlike the known apparatus for optical coherence tomography, according to the invention the optical fiber probe is designed miniature.

Whereas the moving part of the lateral scanner comprises a current conductor and said optical fiber, which is rigidly fastened to the current conductor. The optical fiber serves as a flexible cantilever, its proximal part being fixedly attached to the bearing support. The current conductor is arranged as at least one loop' which envelopes the magnetic system in the area of one of its poles. A part of the optical fiber is placed in the area of said pole of the magnetic system, while the plane of the loop of the current conductor is approximately perpendicular to the direction between the poles of the magnetic system. The current conductor is connected with the source of control current.

In one embodiment, the magnetic system includes a first permanent magnet.

In a particular embodiment, the first permanent magnet is provided with a groove extensive in the direction approximately parallel to the axis of the optical fiber, said optical fiber being placed into said groove.

In another particular embodiment, the magnetic system additionally comprises a second permanent magnet with one pole facing the analogous pole of the first permanent magnet, which is enveloped by the current conductor. Besides, said one pole of the second permanent magnet is located near to the optical fiber.

In another embodiment the second permanent magnet has a groove made in the direction approximately parallel to the axis of the optical fiber.

In a different embodiment the first and second permanent magnets are aligned at their analogous poles, while the optical fiber is placed into a throughhole extending therethrough in a direction approximately parallel to the axis of the optical fiber, the throughhole being formed by facing grooves made in said analogous poles of the permanent magnets.

In another embodiment the current conductor envelopes the second permanent magnet.

It is advisable to shape the magnetic system as a parallelepiped.

In one particular embodiment an output window of the optical fiber probe is arranged near the image plane of the end face of the distal part of the optical fiber. It is advisable to place the outer surface of the output window at the front boundary of the zone of sharp imaging.

In another embodiment the output window of the optical fiber probe is a plane-parallel plate. In the longitudinal throughhole of the body of the optical fiber probe between the lens system and the plane-parallel plate there may be additionally installed a first prism, at least one operating surface of said first prism being antireflection coated.

In a different embodiment the output window of the optical fiber probe is made as a second prism.

It is advisable to make the output window of the optical fiber probe hermetically closed.

In one embodiment the source of control current is placed outside the body of the optical fiber probe.

In another particular embodiment the source of control current is placed inside the body of the optical fiber probe and is designed as a photoelectric converter.

In other embodiments of the optical fiber interferometer it is advisable to make the body of the optical fiber probe as a hollow cylinder, and to use anizotropic single-mode optical fiber.

It is advisable to make changeable a part of the sampling arm of the interferometer, including the part being introduced into an instrumental channel of an endoscope or borescope, the changeable part of said sampling arm being connected by a detachable connection with the main part of the sampling arm.

It is advisable to make disposable the changeable part of the sampling arm of interferometer.

In a particular embodiment the distal end of the optical fiber probe is made with changeable tips.

The developed optical fiber lateral scanner, similarly to described above optical fiber lateral scanner known from U.S. Pat. No. 3,941,927, comprises a stationary part and a moving part. The stationary part includes a bearing support, a magnetic system, and a lens system, said magnetic system comprising a first permanent magnet. The moving part includes a movable current conductor and an optical fiber rigidly fastened to the current conductor. The optical fiber serves as a flexible cantilever and is fixedly attached to the bearing support with a capability for a distal part of said optical fiber of being deflected in a direction approximately perpendicular to its own axis. The end face of the distal part of the optical fiber is optically coupled with the lens system, whereas the current conductor is connected with a source of control current.

Unlike the known optical fiber lateral scanner, according to the invention the current conductor is made as at least one loop, which envelopes the first permanent magnet in the area of one of its poles. A part of the optical fiber is located in the area of said pole of the first permanent magnet, whereas the plane of the loop of the current conductor is approximately perpendicular to the direction between the poles of the first permanent magnet.

In a particular embodiment the first permanent magnet is provided with a groove extensive in a direction approximately parallel to the axis of the optical fiber, said optical fiber being placed into said groove.

In another embodiment the magnetic system additionally comprises a second permanent magnet, with one pole facing the analogous pole of the first permanent magnet, which is enveloped by said current conductor. Besides, said one pole of the second permanent magnet is located near to the optical fiber.

In a different embodiment the permanent magnets are aligned at their analogous poles, whereas the optical fiber is placed into a throughhole extending therethrough in a direction approximately parallel to the axis of the optical fiber, the throughhole being formed by the facing grooves made in said analogous poles of the permanent magnets.

It is advisable to have the current conductor additionally envelope the second permanent magnet.

It is preferable to shape said magnetic system as a parallelepiped.

In one embodiment the optical fiber, bearing support, magnetic system and lens system are elements of an optical fiber probe incorporated into an optical fiber interferometer and are encased into an elongated body with a throughhole extending therethrough, the optical fiber extending through the throughhole. The bearing support, magnetic system and lens system are mechanically connected with the body of the optical fiber probe.

In one embodiment the body of the optical fiber probe is made as a hollow cylinder.

In another particular embodiment an output window of the optical fiber probe is located near the image plane of the end face of the distal part of the optical fiber. It is advisable to place the outer surface of the output window of the optical fiber probe at the front boundary of a zone of sharp imaging.

In a different embodiment the output window of the optical fiber probe is made as a plane-parallel plate. The operating surfaces of the plane-parallel plate are cut at an angle of several degrees relative to the direction of propagation of optical radiation incident on the output window. The inner surface of the plane-parallel plate may be made antireflection coated.

In a particular embodiment a first prism is additionally installed in the longitudinal throughhole in the body of the optical fiber probe between the lens system and the plane-parallel plate. At least one operating surface of this prism is antireflection coated.

In another particular embodiment the output window of the optical fiber probe is made as a second prism. The inner surface of the second prism may be antireflection coated.

It is advisable to make the output window of the optical fiber probe hermetically closed.

In a particular embodiment the bearing support is located in the proximal part of the longitudinal throughhole in the optical fiber probe body. The proximal part of the optical fiber is fastened to the bearing support. The current conductor may be connected with a source of control current via electrodes attached to the bearing support.

In the developed lateral scanner it is advisable to use anizotropic single-mode fiber.

In some embodiments the optical fiber probe is made disposable.

In some other embodiments the distal end of the optical fiber probe is made with changeable tips.

The developed method for studying biological tissue in vivo, similarly to the described above method known from U.S. Pat. No. 5,570,182, comprises the steps of directing a beam of optical radiation in the visible or near IR range towards a biological tissue under study and acquiring subsequently an image of said biological tissue by visualizing the intensity of optical radiation backscattered by biological tissue under study to use said image for diagnostic purpose.

Unlike the known method for studying biological tissue in vivo, according to the invention the biological tissue under study is a biological tissue covered with an epithelium, whereas in the acquired image the basal membrane of said biological tissue is identified, which separates the epithelium from an underlying stroma, and performing diagnostics of said biological tissue under study on basis of the state of the basal membrane.

In a particular embodiment said biological tissue is the biological tissue lining the surface of human cavities and internal organs. When directing the beam of optical radiation towards said biological tissue, a miniature optical fiber probe is inserted into the cavity under study, through which said beam of optical radiation is transmitted from the proximal end of the probe to its distal end, whereas said beam of optical radiation is scanned over said surface under study in compliance with a predetermined rule.

In a particular embodiment in order to insert the miniature optical fiber probe into said human cavity under study, the probe is placed into the instrumental channel of an endoscope.

In another embodiment a low coherent optical radiation beam is used as said optical radiation beam, which is split into two beams. The beam directed towards said biological tissue is the first beam, whereas the second beam is directed towards a reference mirror, the difference in the optical paths for the first and second beams being varied in compliance with a predetermined rule by at least several tens of wavelengths of said radiation. Radiation backscattered from said biological tissue is combined with radiation reflected from the reference mirror. The signal of interference modulation of intensity of the optical radiation, which is a result of this combining, is used to visualize the intensity of optical radiation backscattered from said biological tissue.

In the present invention the moving part of the lateral scanner in the optical fiber probe is designed comprising a current conductor, which envelopes the magnetic system in the area of one of its poles, and an optical fiber, which is rigidly fastened to the current conductor, whereas the optical fiber serves as a flexible cantilever. That allows making smaller the overall dimensions of the optical fiber probe in comparison with known arrangements. The magnetic system includes two permanent magnets aligned at their analogous poles, whereas the optical fiber is placed in a throughhole extending therethrough in a direction approximately parallel to the axis of the optical fiber, the throughhole being formed by the facing grooves made in said analogous poles of the permanent magnets. This configuration ensures optimization of the probe design from the point of view of acquisition of maximum amplitude of deviation of the beam of optical radiation (±1 mm), whereas having limited dimensions of the optical fiber probe, namely, its length is no more than 27 mm, and diameter is no more than 2.7 mm. This allows for making the optical fiber probe as a miniature optical fiber probe, which can be installed in the distal end of the instrumental channel of an endoscope or borescope, the optical fiber probe being incorporated into the sampling arm of the optical fiber interferometer which is part of apparatus for optical coherence tomography. One part of the sampling arm of the optical fiber interferometer is made flexible, thus allowing for inserting it into said channels. Miniature dimensions of the optical fiber probe as well as the flexible arrangement of the sample arm allow to bring up the optical radiation to the hard-to access parts of biological tissue of internal human organs and cavities, including soft biological tissue (for example, human mucosa in gastrointestinal tracts) and hard biological tissue (for example, dental, cartilage and bony tissue). That makes it possible to use the developed apparatus for optical coherence tomography together with devices for visual studying of biological tissue surfaces, for example, with devices for endoscopic studying of human gastrointestinal and urinary tracts, laparoscopic testing of abdominal cavity, observing the process of treatment of dental tissue. Using an output window allows to arrange the optical fiber probe hermetically closed, which, in turn, allows for positioning the optical fiber probe directly on the surface of object under study, in particular, biological tissue. Having the outer surface of the output window at the front boundary of a zone of sharp imaging ensures high spatial resolution (15–20 μm) during scanning of a focused optical beam along the surface of object under study. Arranging the source of control current as a photoelectric transducer and locating it inside the body of the optical fiber probe allows to avoid introducing electrical cords into the instrumental channel. Having antireflection coated inner surface of the output window designed either as a plane-parallel plate or as a prism, allows for a decrease in losses of optical radiation, whereas having beveled operating sides of the plane-parallel plate eliminates reflection from the object-output window boundary. Using anizotropic optical fiber excludes the necessity of polarization control in process of making measurements, whereas using a single-mode optical fiber allows for more simple and lower-cost realization of the device.

In vivo diagnostics of biological tissue covered with epithelium on basis of the state of basal membrane, according to the developed method, allows for early non-invasive diagnostics of biological tissue. The use of the optical fiber probe of the invention, of which the lateral scanner of the invention is a part, allows for diagnostics of the state of biological tissue lining the surface of hard-to-access cavities and internal organs of a patient, for example, by placing the optical fiber probe into an instrumental channel of an endoscope. Using low coherent optical radiation for implementing the developed method ensures high spatial in-depth resolution.

BRIEF DESCRIPTION OF DRAWINGS

The features and advantages of the invention will be apparent from the following detail description of preferred embodiments with reference to the accompanying drawings, in which.

MODES FOR CARRYING OUT THE INVENTION

The operation of the developed apparatus for optical coherence tomography and the developed optical fiber probe will be best understood from the following description of carrying out the method for diagnostics of biological tissue in vivo.

The method for diagnostics of biological tissue in vivo is carried out the following way.

An optical beam in the visible or IR range is directed, for instance, with the aid of a laser, toward a biological tissue under study, the later being a biological tissue covered with epithelium. An image of the biological tissue covered with epithelium is obtained by visualizing the intensity of backscattered optical radiation beam with, for example, a confocal microscope. In the acquired image, the basal membrane is identified, which separates the epithelium from underlying stroma. Diagnostics is made on basis of the state of said basal membrane.

In a specific embodiment, said biological tissue covered with epithelium is a biological tissue lining the surface of cavities and internal organs of a patient. In this case, when directing an optical beam to said biological tissue, a miniature optical fiber probe 8 is inserted into patient's cavity under study (one embodiment of the probe is shown in FIG.

2). It is advisable to place probe 8 at the distal end of the instrumental channel of an endoscope. Said optical radiation beam is transmitted through probe 8 from its proximal end to its distal end. Scanning of said optical radiation beam is performed along the surface under study in accordance with a predetermined rule.

Figure 1:
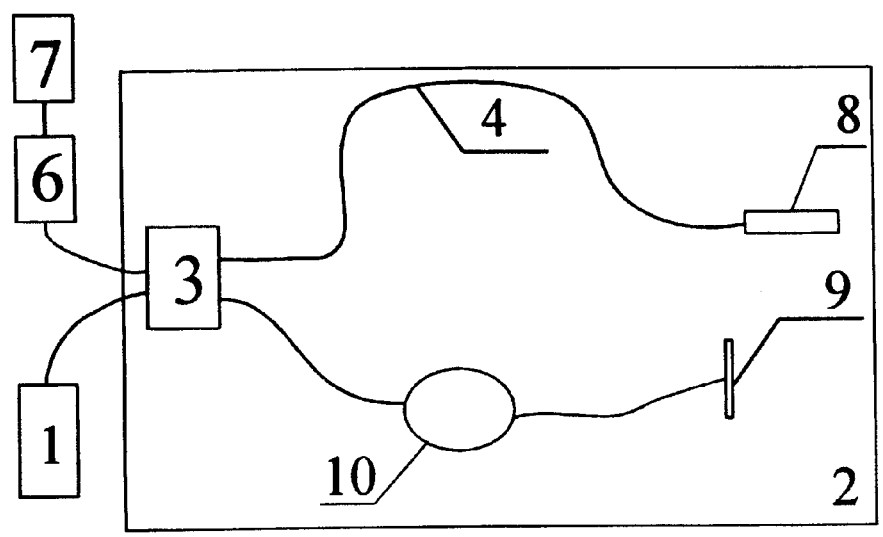
FIG. 1 is a schematic diagram of one particular embodiment of the developed apparatus for optical coherence tomography suitable for implementing the developed method for studying biological tissue in vivo.
Figure 2:
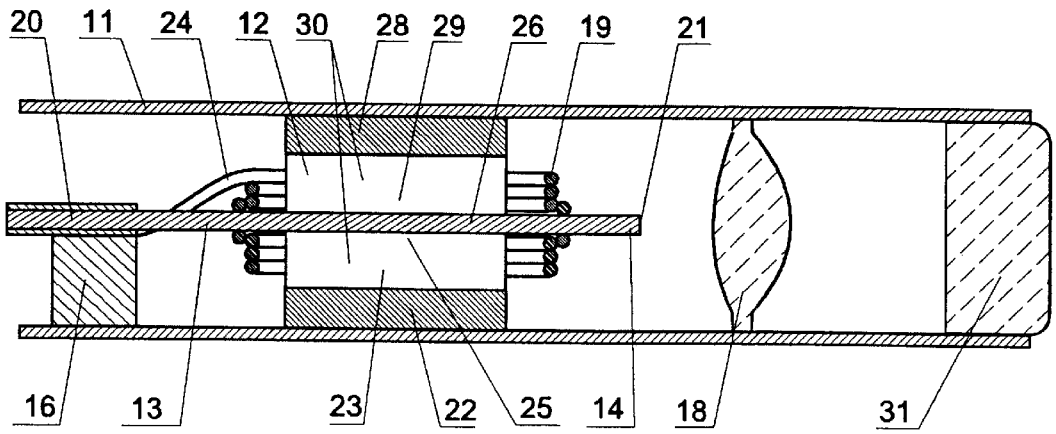
FIG. 2 is a cross-sectional view of one particular embodiment of the developed miniature optical fiber probe.

In a preferred embodiment of the method an optical low coherent radiation beam is used as the optical radiation beam. This embodiment of the developed method may be realized with the aid of the device, a schematic diagram of which is shown in FIG. 1, and with the aid of an optical fiber probe shown in FIG. 2, as follows.

Optical fiber probe 8 is installed at the distal end of the instrumental channel of an endoscope (not shown in the drawing), the outer surface of an output window 31 of optical fiber probe 8 is brought into contact with the biological tissue lining the surface of cavities and internal organs of a patient under study. It must be noted that for some embodiments for better serviceability a part of sampling optical fiber arm 4 of an interferometer 2 may be made changeable, specifically, disposable, and in this case it is connected with the main part of sampling arm 4 by a detachable connection (not shown in the drawing). An optical low coherent radiation beam is formed using a source 1, which can be arranged, for example, as a superluminiscent diode. This optical radiation beam passes to optical fiber interferometer 2, which is a Michelson interferometer, and is then split into two beams by means of a beam-splitter 3 of optical fiber interferometer 2. The first beam is directed toward biological tissue under study using optical fiber sampling arm 4 and optical fiber probe 8. Said beam is scanned over the surface under study in compliance with a predetermined rule using optical fiber probe 8 as follows.

An optical fiber 13, which may be a PANDA-type optical fiber, extends through a throughhole 12 of an elongated body 11 of optical probe 8 and provides for propagation of the first low coheren☐e optical radiation beam from a proximal part 20 of optical fiber 13 to its distal part 14. Body 11 of optical fiber probe 8 may be made of stainless steel. In a particular embodiment the length of body 11 is no more than 27 mm, whereas its diameter is no more than 2.7 mm.

Body 11 comprises also a lateral scanner 15 (see also FIG. 3 and FIG. 4) which is connected with a source of control current (not shown in the drawing). Said source of control current may be located inside body 11 of optical fiber probe 8 and may be arranged as a photoelectric converter (not shown in the drawing). Lateral scanner 15 has a stationary part, which is mechanically connected with body 11 and includes a bearing support 16, magnetic system 17, and lens system 18, and a moving part, which includes a current conductor 19 and optical fiber 13, which serves as a flexible cantilever and is rigidly fastened to current conductor 19 which may be made of insulated copper wire. Referring to FIG. 1, bearing support 16 is placed in the proximal part of a throughhole 12 of body 11, proximal part 20 of optical fiber 13 being fixedly attached to bearing support 16. By the way, bearing support 16 may be located between magnetic system 17 and lens system 18, magnetic system 17 being placed in the proximal part of throughhole 12 of body 11, whereas a middle part of optical fiber 13 is connected with bearing support 16 (this embodiment is not shown in a drawing). A distal part 14 of optical fiber 13 is placed so that it can be deflected in the direction A—A, approximately perpendicular to its own axis. The end face 21 of distal part 14 of optical fiber 13 is optically coupled with lens system 18.

Figure 3:
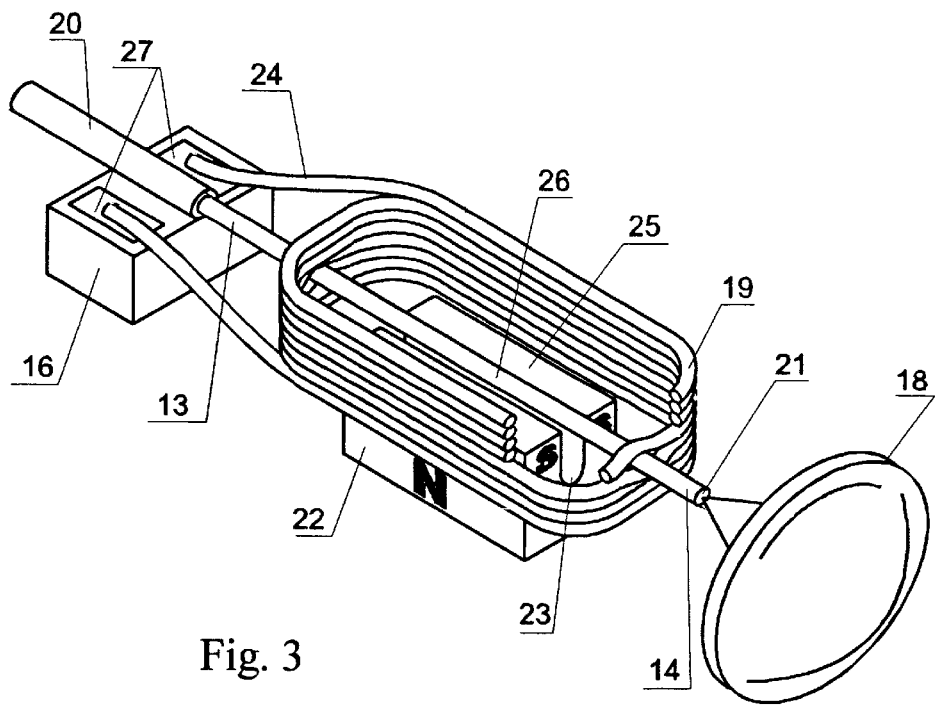
FIGS. 3, 4 are general views of particular embodiments of the developed optical fiber lateral scanner.

Magnetic system 17 of lateral scanner 15 shown in FIG. 3 comprises a first permanent magnet 22, which has a groove 23 extensive in a direction approximately parallel to the axis of optical fiber 13, whereas optical fiber 13 is placed in said groove 23. Current conductor 19 is arranged as at least one loop 24 of wire which envelopes magnetic system 17, i.e., first permanent magnet 22, in the area of one of its poles 25. A part 26 of optical fiber 13 is placed in the area of pole 25. The plane of loop 24 of current conductor 19 is approximately perpendicular to the direction between poles of permanent magnet 22. Current conductor 19 via electrodes 27, which are fixed on bearing support 16, is connected with a source of control current (not shown in the drawing) which is placed outside body 11.

Figure 4:
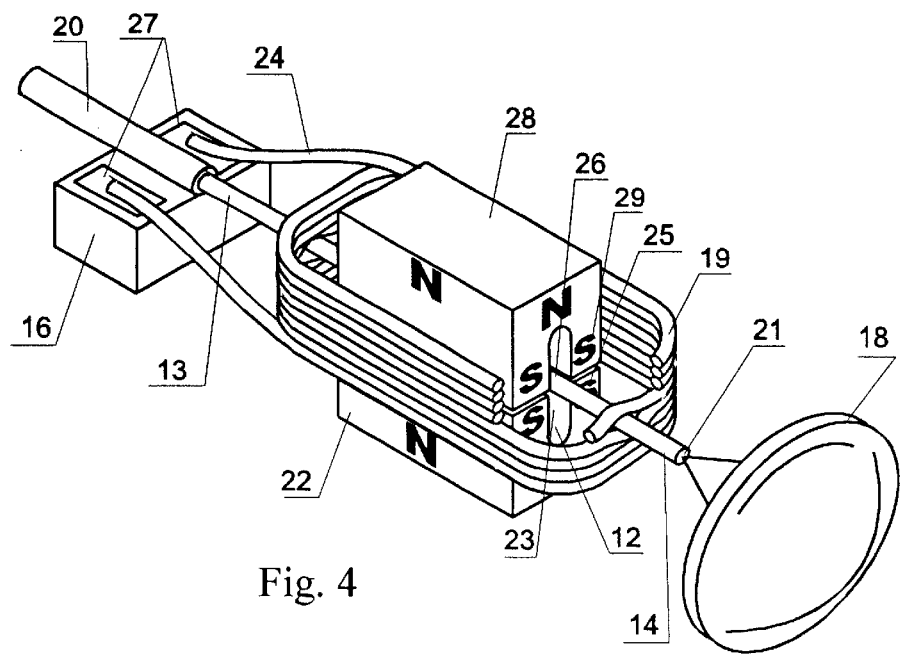

In a particular embodiment of lateral scanner 15 indicated in FIG. 4 magnetic system 17 additionally includes a second permanent magnet 28. First and second magnets, 22 and 28, respectively, are aligned at their analogous poles 25 and 29, whereas magnets 22 and 28 are used to form a stationary magnetic field and may be made from NiFeB material. Optical fiber 13 is placed into a throughhole 30 extending therethrough approximately parallel to the axis of optical fiber 13. The throughhole 30 is formed by facing grooves made in aligned poles 25, 29 of permanent magnets 22 and 28. Diameter of throughhole 30 is determined by predetermined amplitude of deflection of optical fiber 13 with maximum magnetic field intensity in the area of current conductor 19. Current conductor 19 envelopes permanent magnets 22, 28 in the area of their aligned poles 25, 29.

Figure 5:
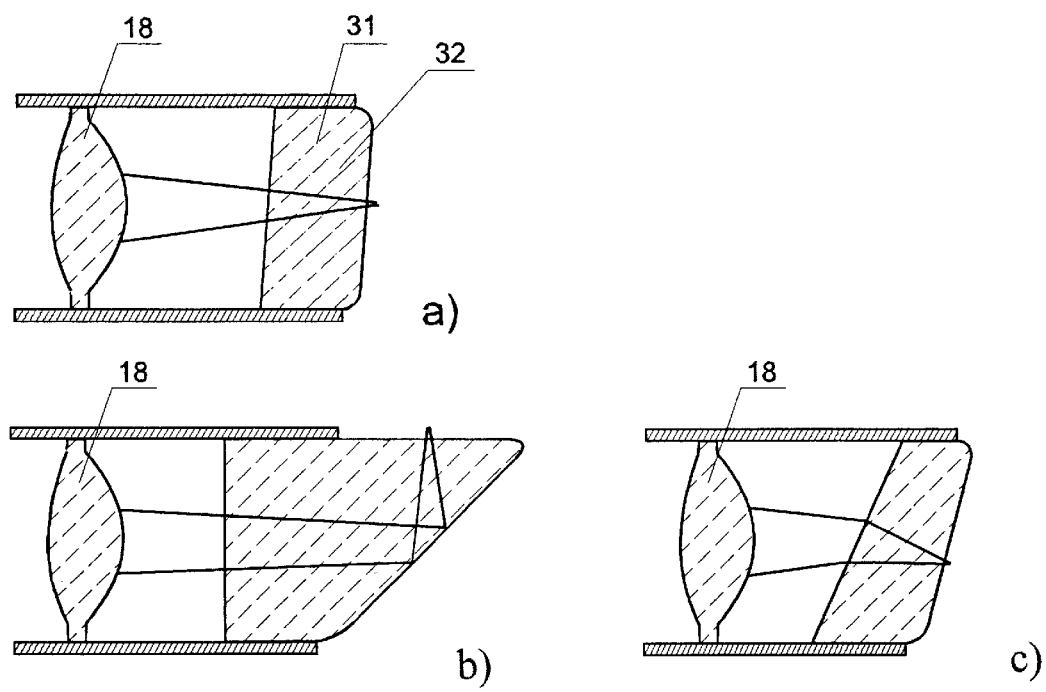
FIGS. 5A, 5B, and 5C are cross-sectional views of particular embodiments of a distal part of the developed optical fiber probe.

An output window 31 of optical fiber probe 8 is placed near to the image plane of end face 21 of distal part 14 of optical fiber 13. In one embodiment shown in FIGS. 4 and 5A, an output window 31 is arranged as a plane-parallel plate 32. Plane-parallel plate 32 is optically transparent in the range of operating frequencies, being made of material allowed for use in medical purposes. Bevel angle of the operating sides of plane-parallel plate 32 relative to the direction of propagation of optical radiation beam incident on output window 31 is determined by a given level of reflections of the optical radiation beam from the front side of plane-parallel plate 32 to the viewing angle of the optical system and must not be more than an angle of divergence of the optical radiation beam. In embodiment shown in FIG. 5A, operating sides of plane-parallel plate 32 are cut at an angle of several degrees relative to the direction of propagation of the optical radiation incident on output window 31. A first prism (not shown in the drawing) may be additionally installed between lens system 18 and plane-parallel plate 32. Referring to FIG. 5B and 5C output window 31 is made as a second prism 33, which may have various configurations. First prism and second prism 33 are used to provide lateral view on surface under study with the aid of optical fiber probe 8. Specific configurations of said prisms are defined by a predetermined angle of lateral view. The values of refractive index of plate 32 and prism 33 are chosen such as to provide a minimum level of reflections from the boundary "output window 31—surface under study" and must be maximally close to the refractive index value of the object under study. The inner surfaces of plane-parallel plate 32 and prism 33 are made antireflection coated in order to decrease losses. The distal part of optical fiber probe 8, which includes output window 31, may be made with changeable tips.

Magnetic system 17 of lateral scanner 15 ensures establishing of a stationary magnetic field. The field lines of the magnetic field induced by magnetic system 17 are situated in the plane of loop 24 of current conductor 19 and cross the loop 24 in the direction approximately orthogonal to the direction of the current in the loop 24 of current conductor 19. So, when control current is applied in current conductor 19, there occurs a force that affects current conductor 19 in the direction approximately orthogonal to the plane of loop 24 of current conductor 19. This force being proportional to the current strength in current conductor 19 and to the intensity of stationary magnetic field induced by magnetic system 17, causes respective movement of current conductor 19. Since the proximal part 20 of optical fiber 13 is fastened in bearing support 16 as a free cantilever, and current conductor 19 is rigidly fixed to optical fiber 13, then when control current is applied in current conductor 19, there occurs a deflection of distal part 14 of optical fiber 13 in the direction approximately perpendicular to its own axis. In a particular embodiment an amplitude of this deflection of distal part 14 of optical fiber 13 is ±0.5 mm. Lens system 18 ensures focusing of the optical radiation beam that has passed through optical fiber 13 onto the surface of biological tissue under study.

The second optical radiation beam by means of reference arm 5 is directed to a reference mirror 9. Reference arm 5 contains an in-depth scanner 10 connected with a source of control voltage (not shown in the drawing). With the aid of in-depth scanner 10 the difference in the optical lengths of arms 4,5 of interferometer 2 is changed at a constant velocity V by at least several tens of operating wavelengths of light source 1.

Referring to FIG. 1, reference mirror 9 is stationary, whereas in-depth scanner 10 is made as an optical fiber piezoelectric transducer known from RU Pat. No. 2,100,787 (U.S. Pat. No. 5,867,268). In this embodiment in-depth scanner 10 comprises at least one body which has piezoelectric properties, exhibits a high perpendicular inverse piezoeffect, and has an electric field vector when an electric field is applied to electrodes, which are mechanically connected with said body, whereas an optical fiber is mechanically connected with said electrodes. A dimension of said piezoelectric body in a direction substantially perpendicular with said electric field vector is essentially larger than a dimension of said body in a direction substantially aligned with said electric field vector. The length of the optical fiber exceeds substantially the diameter of said piezoelectric body.

Figure 6:
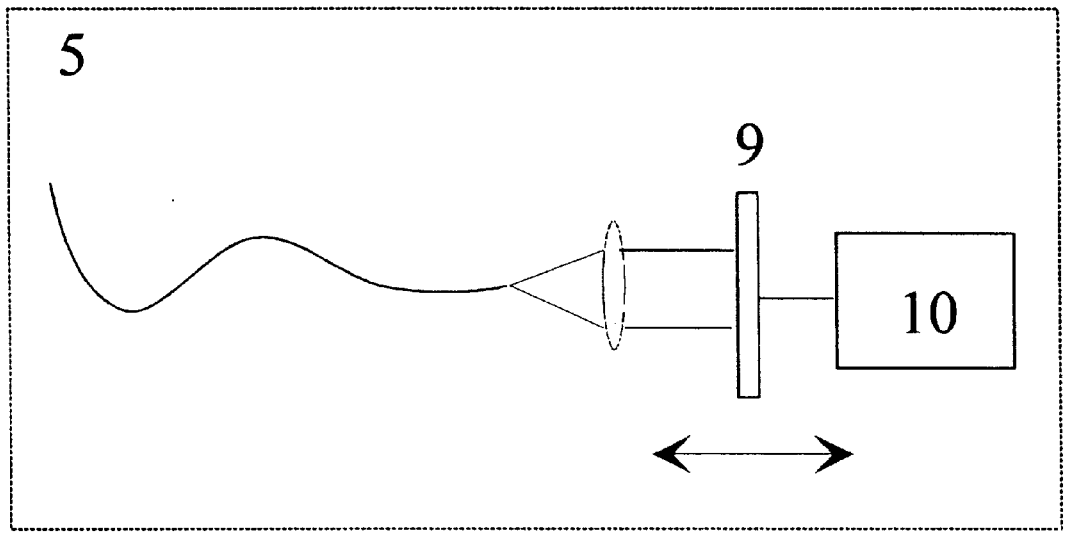
FIGS. 6A and 6B are schematic diagrams of particular embodiments of the interferometer arm comprising an in-depth scanner.
Figure 6:
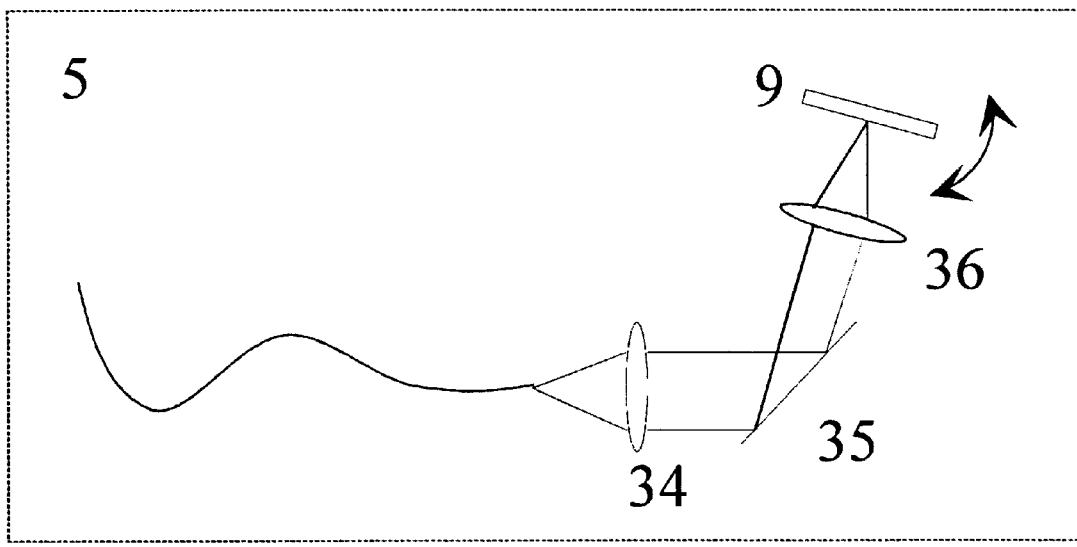

In-depth scanner 10 may be made analogous with in-depth scanners described in U.S. Pat. No 5,321,501. In this case, reference mirror 9 is made movable at a constant speed, and in-depth scanner 10 being connected with reference mirror 9, may be made as mechanisms of different types providing for necessary moving of reference mirror 9 (FIG. 6A).

In-depth scanner 10 may be designed according to the paper by K. F. Kwong, D.Yankelevich et al, "400-Hz mechanical scanning optical delay line"; Optics Letters, Vol. 18, No. 7, Apr. 1, 1993, as a disperse grating delay line (FIG. 6B) comprising a first lens 34, diffraction grating 35 and second lens 36, all these elements being arranged in series along the optical axis. Second lens 36 is optically coupled with reference mirror 9 placed so that it can swing relative to the direction of propagation of incident optical radiation.

Using beam-splitter 3 the radiation backscattered from said biological tissue is combined with the radiation reflected from reference mirror 9. Changing the difference in the optical lengths of arms 4,5 with in-depth scanner 10 leads to interference modulation of intensity of combined optical radiation at the output of beam-splitter 3 at a Doppler frequency f=2V/$\lambda$, where $\lambda$ is the operating wavelength of source 1. Besides, the rule of interference modulation corresponds to the change in the intensity of optical radiation backscattered from biological tissue under study at different depths. Then an image of biological tissue under study is acquired by visualizing intensity of optical radiation backscattered from biological tissue under study by using the signal of interference modulation of intensity of the optical radiation, which is the result of said combining, as follows.

A photodetector 6 provides for conversion of the combined optical radiation from the output of beam-splitter 3 into an electrical signal which arrives at a processing and displaying unit 7. Unit 7 is used to form images of an object under study by visualizing the intensity of back-scattered coherent radiation and may be made, for example, similarly to the data processing and displaying unit discussed in the paper by V. M. Gelikonov et al., "Coherent optical tomography of microinhomogeneities in biological tissues" JETP Lett., v. 61, No 2, pp. 149–153. This data processing and displaying unit comprises a band-pass filter, a log amplifier, an amplitude detector, an analog-to-digital converter, and a computer, all these elements being connected in series. Band-pass filter of unit 7 sorts the signal at a Doppler frequency, thereby improving the signal-to-noise ratio. Once the signal is amplified, it arrives at a detector that sorts a signal proportional to the waveform envelope of this signal. The signal sorted by the amplitude detector of unit 7 is proportional to the signal of interference modulation of intensity of the combined optical radiation. Analog-to-digital converter of unit 7 converts the signal from the output of the amplitude detector into a digital format. Computer of unit 7 provides for acquisition of images by displaying on a video monitor the intensity of the digital signal (said displaying may be performed as described, for instance, in the paper by H. E. Burdick "Digital imaging: Theory and Applications", 304 pp., Me Graw Hill, 1997). Since the digital signal corresponds to the change in intensity of optical radiation backscattered from biological tissue at different depths, the image displayed on the monitor corresponds to an image of biological tissue under study. The biological tissue basal membrane, which separates the epithelium from underlying stroma, is identified in the acquired image. Diagnostics is made on basis of the state of the basal membrane.

Diagnostics of biological tissue with the aid of the method of the invention is illustrated with several clinical cases, whereas the examination of patients took place in hospitals of Nizhny Novgorod (Russia).

Figure 7A:
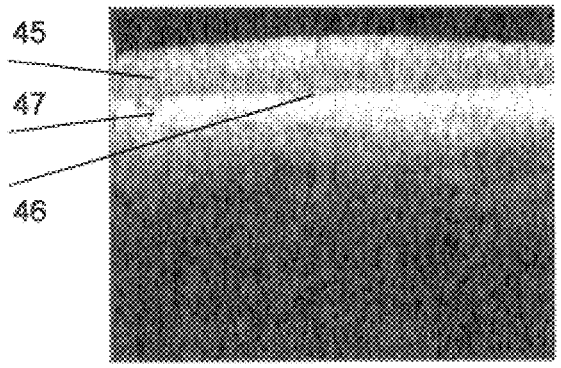
FIGS. 7A, 7B, 7C, 7D, and 7E are images of a uterine cervix obtained by using the developed method.
Figure 7B:
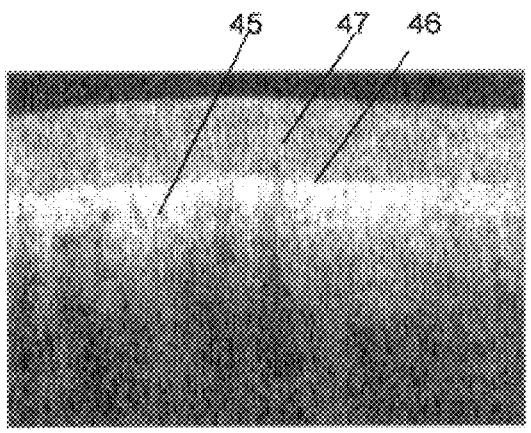

Namely, an examination of women, which had no pathology in the uterine cervix, with the aid of the developed method allowed obtaining images of healthy epithelium of the uterine cervix (FIGS. 7A and 7B). It can be seen from these images that biological tissue covered with healthy epithelium 45 has a smooth basal membrane 46, which separates stratified squamous epithelium 45 from underlying connective tissue 47.

Figure 7C:
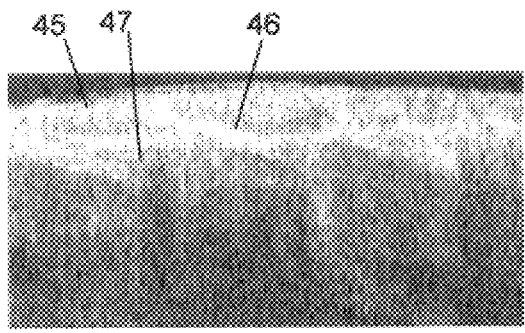
Figure 7D:
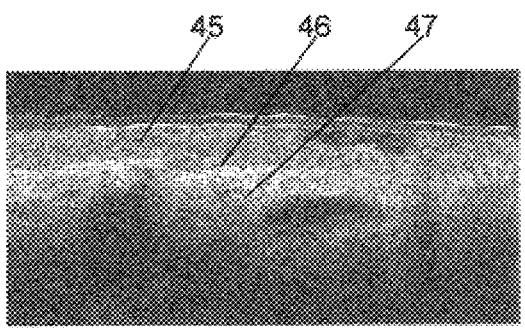

It can be seen from images shown in FIGS. 7C and 7D that pathological regions of biological tissue are characterized by a change in the shape of the basal membrane 46, or violation of its integrity, or its absolute destruction.

FIG. 7C shows an image of a pathological region of the uterine cervix, obtained with the aid of the developed method, of a female patient I., 31 years old, in which there can be seen appendages of the basal membrane 46 in an arc form, i.e. an alteration of the shape of the basal membrane 46 not affecting its integrity. The clinical diagnostics of female patient I was precancer of uterine cervix. Standard colposcopy technique revealed a phenomenon known as so-called mosaic. Information obtained with target biopsy and subsequent morphological study of biopsy material provided grounds for diagnosing cervical intraepithelial neoplasia of the II degree.

FIG. 7D shows an image of a pathological region of the uterine cervix, obtained with the aid of the developed method, of a female patient G., 25 years old, in which there can be distinctly indicated structural changes in stratified squamous epithelium 45 and different extents of changes in the basal membrane 46. Female patient G was admitted to the clinic for a suspicion for uterine cervix cancer T1a. During the further course of treatment the patient underwent conization (i.e., conical removal of pathological region) in the uterine cervix. Based on the results of morphological study of the removed material the diagnostics was made as follows: cervical intraepithelial neoplasia of the III degree with transition into cancer in situ and microcarcinoma. It is well known from morphological research that exactly this stage in the development of malignant process originating in the basal and parabasal layers of cells is accompanied by alterations in shape and an occurrence of microruptures of the basal membrane.

Figure 7E:
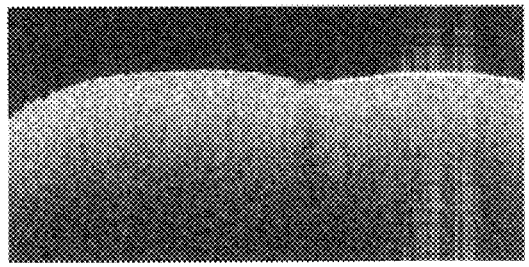

FIG. 7E presents a tomographic image of a tumor region where the basal membrane is not seen. This image was obtained with an examination of a female patient M., 66 years old that was admitted to the clinic for uterine cervix cancer T1b. This diagnostics was made clinically and confirmed morphologically based on the results of biopsy.

Thus, the above examples demonstrate a possibility for using the developed method for studying biological tissue in vivo in diagnostics of different stages of uterine cervix cancer.

Figure 8:
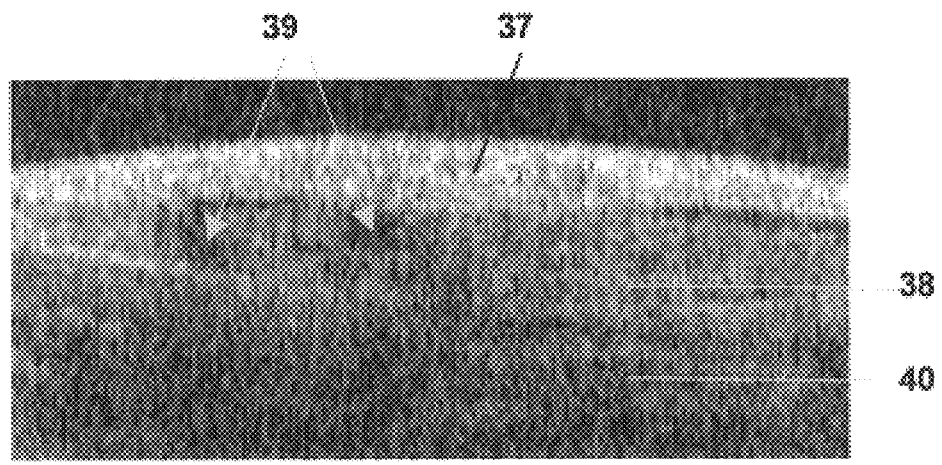
FIG. 8A shows a tomographic image of a front abdominal wall.
FIG. 8B shows the structure of a tooth with a compomer filling.
Figure 8:
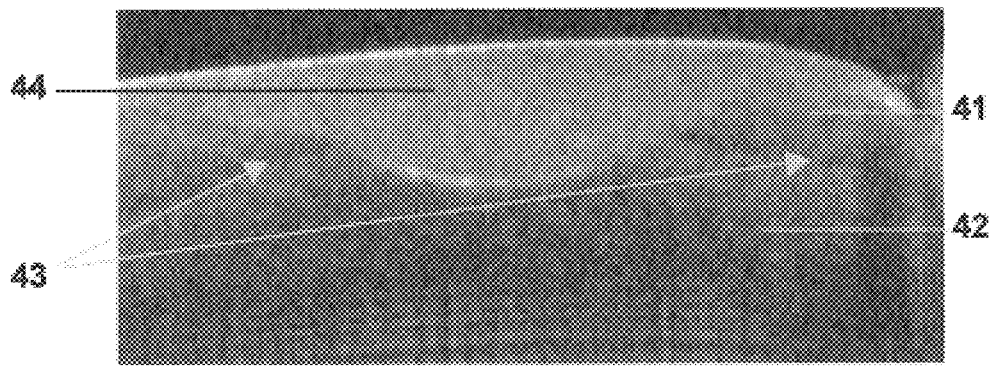

FIG. 8A and FIG. B illustrate opportunities to obtain images of other human biological tissues with the aid of the apparatus and lateral scanner of the present invention. In particular, FIG. 8A demonstrates a tomographic image of a front abdominal wall obtained during a laporoscopic examination of a female patient E., 22 years old. On this tomographic image one can see the serous membrane 37 with a layer of connective tissue, characterized by high reflectivity of optical radiation, the subserous layer 38 including loose connective tissue and blood vessels 39, characterized by low reflectivity of optical radiation, and underlying muscle layers 40.

FIG. 8b shows a tomographic image of a tooth of a patient K., 56 years old, on which one can distinctly see the enamel 41, dentine 42, the boundary enamel-dentine 43 and a compomer filling 44.

INDUSTRIAL APPLICABILITY

The invention can be applied for medical diagnostics of individual organs and systems of human body in vivo, for example, of hard-to-access cavities and internal organs, as well as for industrial diagnostics, for instance, for control of technological processes. It should be noted that the invention can be implemented with using standard means.

What is claimed is:

1. An apparatus for optical coherence tomography comprising:
    a low coherent light source;
    an optical fiber interferometer, including a beam-splitter, a sampling and reference optical fiber arms, and a photodetector, which are mutually optically coupled, a data processing and displaying unit, a reference mirror being placed at the end of said reference arm, the output of said photodetector being connected with said data processing and displaying unit, and a source of control voltage, whereas the output of said data processing and displaying unit of said optical fiber interferometer is the output of said apparatus for optical coherence tomography;
    at least one of said arms comprising an in-depth scanner having a capability of changing the optical length of said arm by at least several tens of operating wavelengths of said light source, said in-depth scanner being controlled by a source of control voltage, said sampling arm including a flexible part, which is made capable of being introduced into an instrumental channel of an endoscope or borescope and being provided with an optical fiber probe;
    said optical fiber probe being designed miniature and including an elongated body with a throughhole extending therethrough and a lateral scanner comprising a stationary part and a moving part, an optical fiber extending through said throughhole;
    said stationary part being mechanically connected with said body of said optical fiber probe and including a bearing support, a magnetic system, and a lens system;
    said moving part of said lateral scanner including a current conductor and said optical fiber;
    said optical fiber being rigidly fastened to said current conductor and serving as a flexible cantilever, its proximal part being fixedly attached to said bearing support, a distal part of said optical fiber allowing for being deflected in the direction approximately perpendicular to its own axis, and an end face of said distal part of said optical fiber being optically coupled with said lens system;
    said current conductor being arranged as at least one loop, enveloping said magnetic system in the area of one of its poles, with a part of said optical fiber being placed in the area of said pole of said magnetic system, and the plane of said loop of said current conductor being approximately perpendicular to the direction between the poles of said magnetic system; and
    said lateral scanner being controlled by a source of control current, and said current conductor being connected with said source of control current.

2. An apparatus as claimed in claim 1, wherein said magnetic system includes a first permanent magnet.

3. An apparatus as claimed in claim 2, wherein said magnetic system additionally comprises a second permanent magnet with one pole facing the analogous pole of said first permanent magnet, which is enveloped by said current conductor, whereas said one pole of said second permanent magnet is located near to said optical fiber.

4. An apparatus as claimed in claim 2, wherein one of said permanent magnets is provided with a groove extensive in a direction approximately parallel to the axis of said optical fiber, said optical fiber being placed into said groove.

5. An apparatus as claimed in claim 3, wherein said first and second permanent magnets are provided each with a groove extensive in a direction approximately parallel to the axis of said optical fiber, said first and said second permanent magnets being aligned at their analogous poles, whereas said optical fiber is placed into a throughhole extending therethrough in a direction approximately parallel to the axis of said optical fiber, said throughhole being formed by said facing grooves made in said analogous poles of said permanent magnets.

6. An apparatus as claimed in claim 5, wherein said current conductor envelopes additionally said second permanent magnet.

7. An apparatus as claimed in claim 1, wherein an output window of said optical fiber probe is arranged near the image plane of said end face of said distal part of said optical fiber, the outer surface of said output window of said optical fiber probe being located at the front boundary of a zone of sharp imaging.

8. An apparatus as claimed in claim 7, wherein said output window of said optical fiber probe is made as a plane-parallel plate.

9. An apparatus as claimed in claim 7, wherein said output window of said optical fiber probe is made as a second prism.

10. An apparatus as claimed in claim 7, wherein said output window of said optical fiber probe is hermetically closed.

11. An apparatus as claimed in claim 1, wherein said the source of control current is placed outside said body of said optical fiber probe.

12. An apparatus as claimed in claim 1, wherein said source of control current is placed inside said body of said optical fiber probe and is designed as a photoelectric converter.

13. An apparatus as claimed in claim 1, wherein said optical fiber is anizotropic.

14. An apparatus as claimed in claim 1, wherein said optical fiber is single-mode.

15. An apparatus as claimed in claim 1, wherein a part of said sampling arm of said interferometer, including said part that is made capable of being introduced into an instrumental channel of an endoscope or borescope, is made changeable and is connected by a detachable connection with a main part of said sampling arm.

16. An apparatus as claimed in claim 15, wherein said changeable part of said sampling arm of said interferometer is made disposable.

17. An apparatus as claimed in claim 1, wherein the distal part of said optical fiber probe is made with changeable tips.

* * * * *

UNITED STATES PATENT AND TRADEMARK OFFICE
CERTIFICATE OF CORRECTION

PATENT NO. : 6,608,684 B1
DATED : August 19, 2003
INVENTOR(S) : Valentin M. Gelikonov et al.

It is certified that error appears in the above-identified patent and that said Letters Patent is hereby corrected as shown below:

Title page, Item [54] and Column 1, lines 1-4,
Title, please delete "OPTICAL COHERENT TOMOGRAPHY APPARATUS, FIBEROPTIC LATERAL SCANNER AND METHOD FOR STUDYING BIOLOGICAL TISSUES IN VIVO", and insert therefor -- OPTICAL COHERENCE TOMOGRAPHY APPARATUS, OPTICAL FIBER LATERAL SCANNER AND METHOD FOR STUDYING BIOLOGICAL TISSUES IN VIVO --.

Title page,
Item [57], ABSTRACT,
Line 8, please delete "," (comma).

Signed and Sealed this

Twentieth Day of January, 2004

JON W. DUDAS
*Acting Director of the United States Patent and Trademark Office*